United States Patent
Henzler et al.

(10) Patent No.: US 8,232,369 B2
(45) Date of Patent: Jul. 31, 2012

(54) DEVICE AND METHOD FOR PRECIPITATION OF PEPTIDES

(75) Inventors: Hans-Jürgen Henzler, Solingen (DE); Stephan Kirchner, Wuppertal (DE); Dirk Havekost, Köln (DE); Klaus Kaiser, Bergisch Gladbach (DE); Jörg Kauling, Köln (DE); Richard Pasquinelli, Benson, NC (US); Rolf Treckmann, Bergisch-Gladbach (DE)

(73) Assignees: Talecris Biotherapeutics, Inc.NC (US); Bayer Technology Services GmbH, Leverkusen (DE)

( * ) Notice: Subject to any disclaimer, the term of this patent is extended or adjusted under 35 U.S.C. 154(b) by 43 days.

(21) Appl. No.: 12/520,117

(22) PCT Filed: Nov. 27, 2007

(86) PCT No.: PCT/US2007/085580
§ 371 (c)(1),
(2), (4) Date: Dec. 23, 2009

(87) PCT Pub. No.: WO2008/079571
PCT Pub. Date: Jul. 3, 2008

(65) Prior Publication Data
US 2010/0093982 A1    Apr. 15, 2010

Related U.S. Application Data

(60) Provisional application No. 60/871,514, filed on Dec. 22, 2006.

(51) Int. Cl.
*C07K 1/30*    (2006.01)

(52) U.S. Cl. .......... 530/344; 530/419; 422/255
(58) Field of Classification Search .......... None
See application file for complete search history.

(56) References Cited

U.S. PATENT DOCUMENTS

| | | | |
|---|---|---|---|
| 2,390,074 A | | 2/1942 | Cohen |
| 4,066,549 A | * | 1/1978 | Oeser et al. .......... 210/177 |
| 2004/0019014 A1 | * | 1/2004 | Gustavsson et al. .......... 514/60 |

OTHER PUBLICATIONS

Chan et al., "The Kinetics of Protein Precipitation by Different Reagents", Biotechnology and Bioengineering, vol. 28, pp. 387-393, 1986.

Chang, Chong E., "Continuous Fractionation of Human Plasma Proteins by Precipitation from the Suspension of the Recycling Stream", Biotechnology and Bioengineering, vol. 31, pp. 841-846, 1988.

Cohn et al., "Preparation and Properties of Serum and Plasma Proteins, IV. A System for the Separation into Fractions of the Protein and Lipoprotein Components of Biological Tissues and Fluids 1a,b,c,d", Department of Physical Chemistry, vol. 68, pp. 459-475, Mar. 1946.

Raphael et al., "Isoelectric Precipitation of Sunflower Protein in a Tubular Precipitator", The Canadian Journal of Chemical Engineering, vol. 73, pp. 470-483, Aug. 1995.

* cited by examiner

*Primary Examiner* — Karlheinz R Skowronek
*Assistant Examiner* — Roy Teller
(74) *Attorney, Agent, or Firm* — Norris McLaughlin & Marcus, P.A.

(57) ABSTRACT

The present invention relates to a method for precipitation of peptide where the mixing step of the peptide with the precipitation aid and the precipitation itself are specially separated.

13 Claims, 8 Drawing Sheets

DEVICE AND METHOD FOR PRECIPITATION OF PEPTIDES

This application is a 371 of PCT/US2007/085580, filed Nov. 27, 2007, which claims priority benefit under 35 U.S.C. §119(e) of the U.S. Provisional Application No. 60/871,514 filed Dec. 22, 2006.

The present application is related to the field of devices and methods for the precipitation of peptides and proteins.

In the course of the isolation of peptides and proteins, e.g. from body tissues or from bacterial cell cultures, various peptide or protein precipitation methods are known in the art.

Especially in the field of plasma proteins for clinical use there exists an industrial fractionation process (the so-called Cohn-process, E. J. Cohn et al, J. Chem. Am. Soc. 68, 1946, 459 and U.S. Pat. No. 2,390,074 which are hereby incorporated by reference) which involves a number of batch processing steps including operations like precipitation and centrifugal separation or filtration of the precipitated proteins. The separation and the yield are improved by a larger and more uniform particle size of the precipitate. In this context, regard is also given to Chan et al. Biotech. Bioeng. XXVIII (1986), 387-393, Chang, Bioeng. 31 (1988), 841-846, Raphael et al. Can. J. Chem. Eng. 73 (1005), 471-483 and U.S. Pat. No. 4,067,863, which are all incorporated by reference.

However, since these properties are generally impaired by super saturation of the precipitant (ethanol EtOH or/and buffer) in consequence of insufficient mixing and excessive particle stress, it has been shown for many applications that conventional batch reactors are not optimal, where the mixing of the precipitant, the precipitation, the growth and the ripening of particles is carried out all in one stirred tank. Another result of insufficient mixing may be additional yield loss due to over heating (heat of dissolution) and harmful pH values.

It is therefore an object of the present invention to provide a method for the precipitation for peptides and/or proteins, which allows for many applications a more controlled precipitation with higher yields.

Such a method is disclosed in claim 1 of the present invention. Accordingly, a method for the precipitation for peptides is disclosed comprising the steps of
  a) a first mixing step of an aqueous peptide solution with a precipitation aid and
  b) a precipitation step in order to precipitate the peptide,
whereby steps a) and b) are carried out spacially separated from each other.

The term "spacially separated" especially means and/or includes that the steps a) and b) are carried out in two different vessels (which are connected with each other via pipes etc.); however, the term "spacially separated" also especially means and/or includes that the steps a) and b) may be carried out in two separated parts of one vessel, e.g. a fluid reactor.

The term "precipitation aid" especially includes and/or means any chemical compound or any mixture of chemical compounds which are able to adjuve or to cause the precipitation of peptides out of aqueous solution. According to a preferred embodiment of the present invention, the precipitation aid is selected out of the group of organic solvents comprising ethanol, salt solutions, acids, pH-buffers, phenol, non ionic polymers, ionic polyelectrolytes or mixtures thereof.

The term "peptides" especially includes also substituted and unsubstituted peptides and/or proteins, the substitutions may be—but not limited to—glycosides, nucleic acids, alkyl groups, aryl groups or mixtures thereof, whereby the peptide backbone and/or the side groups may be substituted.

By using this method, within a wide range of applications at least one or more of the following advantages may be reached:
  A reduction of fluctuation in concentration as well as stresses in the particles
  The possibility of systematically adjusting the relative saturation and the avoidment of excessive supersaturation
  Due to the above, in many applications a better separability of different peptides which are possibly contained in one solution may be reached
  A reduced peptide damage
  A reduced process time
  Higher yields and quality of the precipated peptide
  A reduction of the "scale-up" problem According to an embodiment of the present invention, the macroscopic mixing time in step a) is $\geq 1$ ms and $\leq 1000$ ms, according to an embodiment of the present invention, the macroscopic mixing time in step a) is $\geq 10$ ms and $\leq 100$ ms According to an embodiment of the present invention, the average mixing velocity (average velocity inside the mixing tube) in step a) is $\geq 0.05$ m/s and $\leq 5$ m/s. This may help within a wide range of applications to keep the time in step a) as little as possible. According to an embodiment of the present invention, the average mixing velocity in step a) is $\geq 0.2$ m/s and $\leq 1.5$ m/s, according to an embodiment of the present invention, the average mixing velocity in step a) is $\geq 0.3$ m/s and $\leq 1$ m/s.

According to an embodiment of the present invention, the pressure drop inside the jet mixer in step a) $\Delta p$ is $\geq 0.05$ bar and $\leq 20$ bar. This has been shown within a wide range of applications with the present invention to further improve step a). According to an embodiment of the present invention, in step a) $\Delta p$ is $\geq 0.1$ bar and $\leq 2.5$ bar. according to an embodiment of the present invention, in step a) $\Delta p$ is $\geq 0.2$ bar and $\leq 1$ bar.

According to an embodiment of the present invention, step a) is performed in a jet mixer with at least two inlets, one for the peptide solution and the precipitation aid, respectively.

In this regard it is especially preferred that the ratio d1 (the diameter of the inlet of the peptide solution) to D (which is the width of the mixing chamber) is $\geq 0.1:1$ and $\leq 0.4:1$, more preferred $\geq 0.2:1$ and $\leq 0.3:1$.

In this regard it is especially preferred that the ratio d2 (the diameter of the inlet of the precipitation aid) to D (which is the width of the mixing chamber) is $\geq 0.05:1$ and $\leq 0.3:1$, more preferred $\geq 0.08:1$ and $\leq 0.13:1$.

According to an embodiment of the present invention step b) is performed while continuously agitating with at least one impeller producing marginal particle stress. According to an embodiment of the present invention step b) is performed while continuously agitating with at least one blade agitator. It has been shown in a wide range of applications within the present invention that this may help to improve the precipitation in step b)

The term "blade agitator" especially means or includes that several radial orientated blades with no inclination to the vertical may be provided on a common axis; if such a blade agitator is used, it is especially preferred that the number of blades is $\geq 3$ and $\leq 9$, preferably $\geq 4$ and $\leq 6$.

According to an embodiment of the present invention, step b) is performed while continuously and/or interrupted agitating or agitating with stepwise changed agitation power with $\geq 0.01$ W/m$^3$ and $\leq 50$ W/m$^3$. Such a measure has shown in practice for a wide range of applications to lead to a good precipitation behaviour of the peptide, especially leading to a bigger average size of a more stable precipitate. According to an embodiment of the present invention, step b) is performed while agitating with $\geqq 0.1$ W/m$^3$ and $\leqq 20$ W/m$^3$, according to an embodiment of the present invention, step b) is performed while agitating with $\geqq 1.5$ W/m$^3$ and $\leqq 5$ W/m$^3$ According to an embodiment of the present invention, step b) is performed while agitating with an agitator having no inclined blades and therefore mainly producing radial flow.

According to an embodiment of the present invention, the agitator is set with an extrentricity of $\geqq 0$ and $\leqq 0.15$. The term excentricity in the context of the present invention especially means and or includes the term e/D with e being the distance from the edge of the agitator to the wall of the vessel and/or the compartment where step b) is performed and D being the diameter of the vessel and/or the compartment where step b) is performed.

Such a measure has shown in practice for a wide range of applications to improve the precipitation as well, since then the mixing behaviour of the agitator may be greatly enhanced.

According to an embodiment of the present invention, the agitator is set with an extrentricity of $\geqq 0.1$ and $\leqq 0.05$, according to an embodiment of the present invention, the agitator is set with an extrentricity of $\geqq 0.03$ and $\leqq 0.015$.

According to an embodiment of the present invention, the ratio of the blade diameter d to the diameter D of the vessel and/or the compartment where step b) is performed is d:D$\geqq 0.4$:1 and $\leqq 0.7$:1. By doing so, a continuously improved stirring behaviour with decreasing particle stress of the agitator can be ensured for a wide range of applications within the present invention.

According to an embodiment of the present invention, the ratio of the blade diameter d to the diameter D of the vessel and/or the compartment where step b) is performed is d:D$\geqq 0.45$:1 and $\leqq 0.65$:1, According to an embodiment of the present invention, d:D is $\geqq 0.5$:1 and $\leqq 0.6$:1

According to an embodiment of the present invention, the blade height to diameter ratio of the at least one blade agitator is h:d$\geqq 0.15$:1 and $\leqq 1.3$:1. with h being the height and d being the diameter. In case the blade agitator comprises several blades it is especially preferred that all of the blades obey this ratio. According to an embodiment of the present invention, the height:width ratio of the blade(s) of the blade agitator is h:d$\geqq 0$, 25:1 and $\leqq 1$:1.

According to an embodiment of the present invention, the ratio of the vessel and/or the compartment where step a) is performed towards the vessel and/or the compartment where step b) is performed is $\geqq 0.01$:1 and $\leqq 0.1$:1. It has been surprisingly shown that for a wide range of applications it may be advantageous to have a relatively small mixing chamber (i.e. the vessel where step a) is performed) in relation to the precipitation vessel, since then the precipitation aid may be present in a rather great excess during step a).

According to an embodiment of the present invention, the ratio of the vessel and/or the compartment where step a) is performed towards the vessel and/or the compartment where step b) is performed is $\geqq 0.02$:1 and $\leqq 0.08$:1.

According to an embodiment of the present invention, the method comprises a step a1) between steps a) and b):
a1) performing a first agglomerate formation and/or a heat exchange in order to remove heat of mixing of step a)

This has been shown to be advantageous for a wide range of applications within the present invention since then a deterioration or denaturation of the protein may be avoided.

According to an embodiment of the present invention, the method comprises a step c) after steps a) and b):
c) constantly and/or discontinuously delivering a part of the solution of the precipitation suspension out of step b) to be co-admixed in step a)

By doing so, within a wide range of applications the precipitation step may be run continuously or batch-like which may help to improve the precipitation of the peptide.

According to an embodiment of the present invention, the method comprises a step a2) and a3) between steps a1) and b):
a2) admixing further precipitation aid and
a3) optionally repeating steps a1) and a2) ad lib.

The invention furthermore relates to a device for carrying out the method according to the invention.

The aforementioned components, as well as the claimed components and the components to be used in accordance with the invention in the described embodiments, are not subject to any special exceptions with respect to their size, shape, material selection and technical concept such that the selection criteria known in the pertinent field can be applied without limitations.

Additional details, characteristics and advantages of the object of the invention are disclosed in the subclaims and the following description of the respective figures—which in an exemplary fashion—show several preferred embodiments of devices for performing the method according to the invention.

Figure 1:
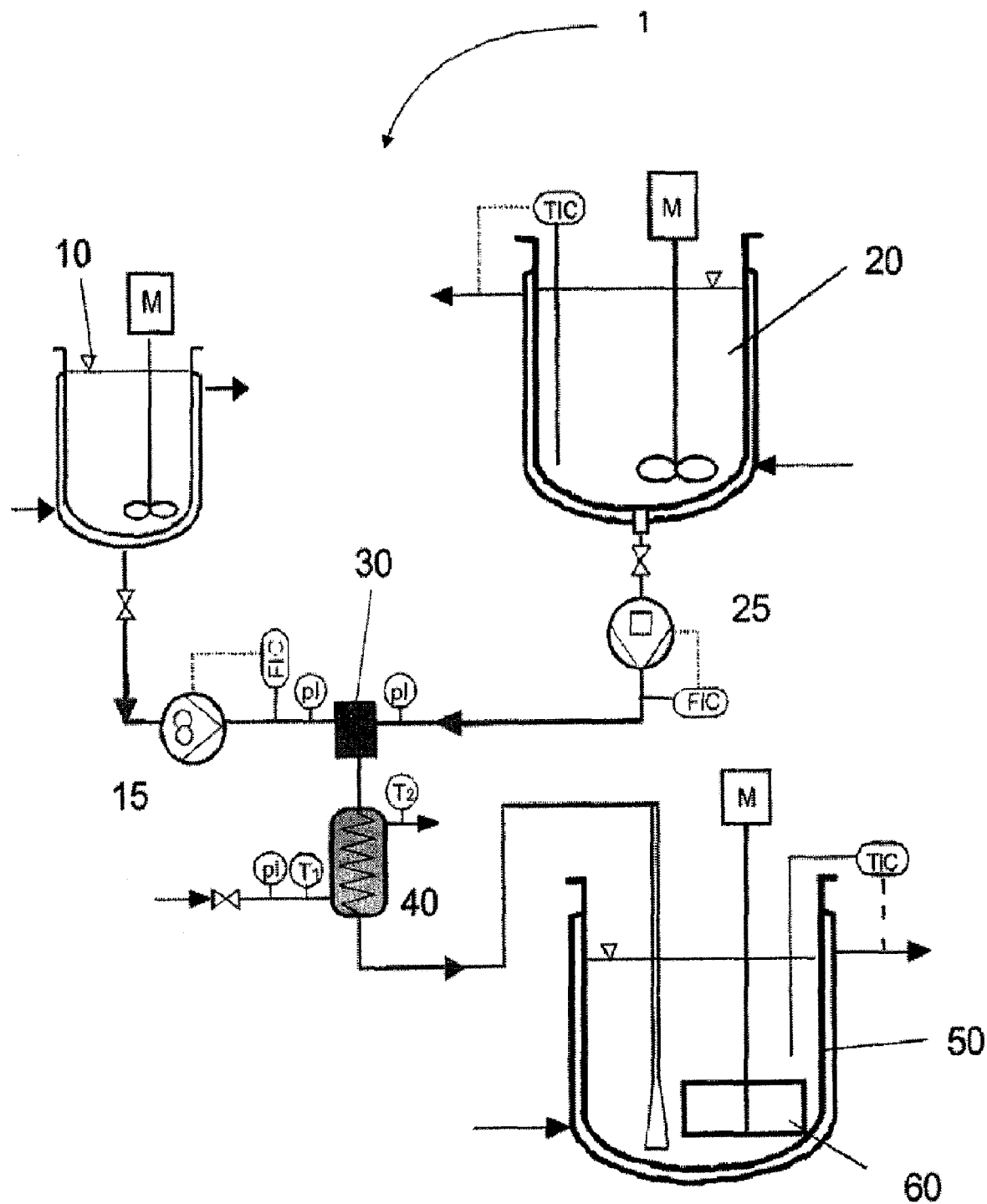
FIG. 1 shows a very schematical view of a device for performing the method according to the invention according to a first embodiment of the present invention.

FIG. 1 shows a very schematical view of a device 1 for performing the method according to the invention according to a first embodiment of the present invention. This device comprises a first vessel 10 where the precipitation aid is provided, which is connected via a first pump 15 to a jet mixer 30, where step a) of the method is performed.

A second vessel 20, where the peptide to be precipitated (e.g. in an aqueous solution together with other body fluids such as carbohydrates, nucleic acids etc.) is provided, is also in connected to the jet mixer 30 via a second pump 25.

In the jet mixer 30, step a) of the method according to the present invention is carried out; the mixing step is preferably performed as previously described. After the mixing step, at least some of the heat is removed by the heat exchanger 40 and then the mixture is delivered into the precipitation vessel 50.

It should be noted that FIG. 1 is in this context very schematic and in the actual application the situation will most likely a bit different.

It is according to an embodiment of the present invention especially preferred that the tube which delivers the mixture into the vessel ends up in a "trumpet-like" section with an angle of is $\geq 2°$ and $\leq 8°$.

In the precipitation vessel, and blade agitator 60 is provided which is preferably as described above.

Figure 2:
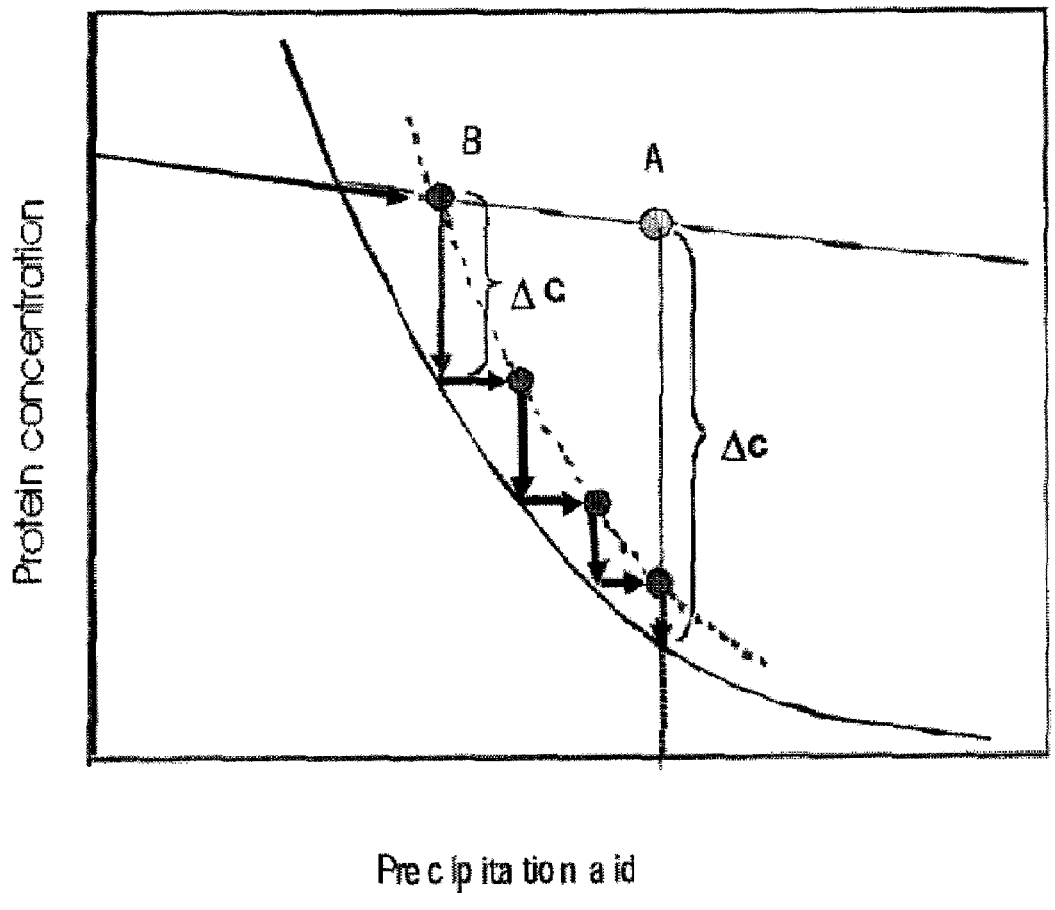
FIG. 2 shows a very schematical diagram showing the protein concentration vs. the amount of precipitation aid for the recirculation mode ("B") and the batch precipitation mode ("A")

FIG. 2 shows a very schematical diagram showing the protein concentration vs. the amount of precipitation aid for the recirculation mode ("B") and the batch precipitation mode ("A"). In this diagram, the solid curve represents the solubility of protein in the solution.

Although not limited to this, the inventors have in practice so far the present invention in essentially two modes, the batch precipitation mode ("A") and the recirculation mode ("B").

In the batch precipitation mode, a vast excess of precipitation aid is added to the protein solution at once, which will lead to point "A" in the diagram. The amount of supersaturation ($\Delta c$) will lead to almost immediate precipitation of the protein. Since the mixing step a) is fast in relation to the second step b), this can be used within a wide range of applications to speed up the precipitation process.

In the recirculation mode ("B"), only a small excess of precipitation aid is added. Therefore the smaller $\Delta c$ will cause only a partial precipitation of the protein (as indicated in the diagram). Again, some more precipitation aid is added, and the precipitation awaited. In the end, the sequel of addition-precipitation-addition-precipitation etc. will ideally occur between the saturation curve c* (straight line) and the dotted line.

This recirculation mode has for some applications the advantage that the precipitated peptide will sometimes be more clean, since co-precipitation can be avoided. The reduced over saturation $\Delta c/c^*$ may lead to an increase of the ratio: particle growth to nucleation velocity and may therefore improve the precipitation result.

In this particular embodiment, the precipitation vessel 50 is connected via a line 70 (see FIG. 4) with the connection between the vessel 20 (which contains the peptide) and the jet mixer 30. This allows to take out continuously a part of the mixture inside vessel 50 in order to mix it once again with the precipitation aid 10.

Figure 3:
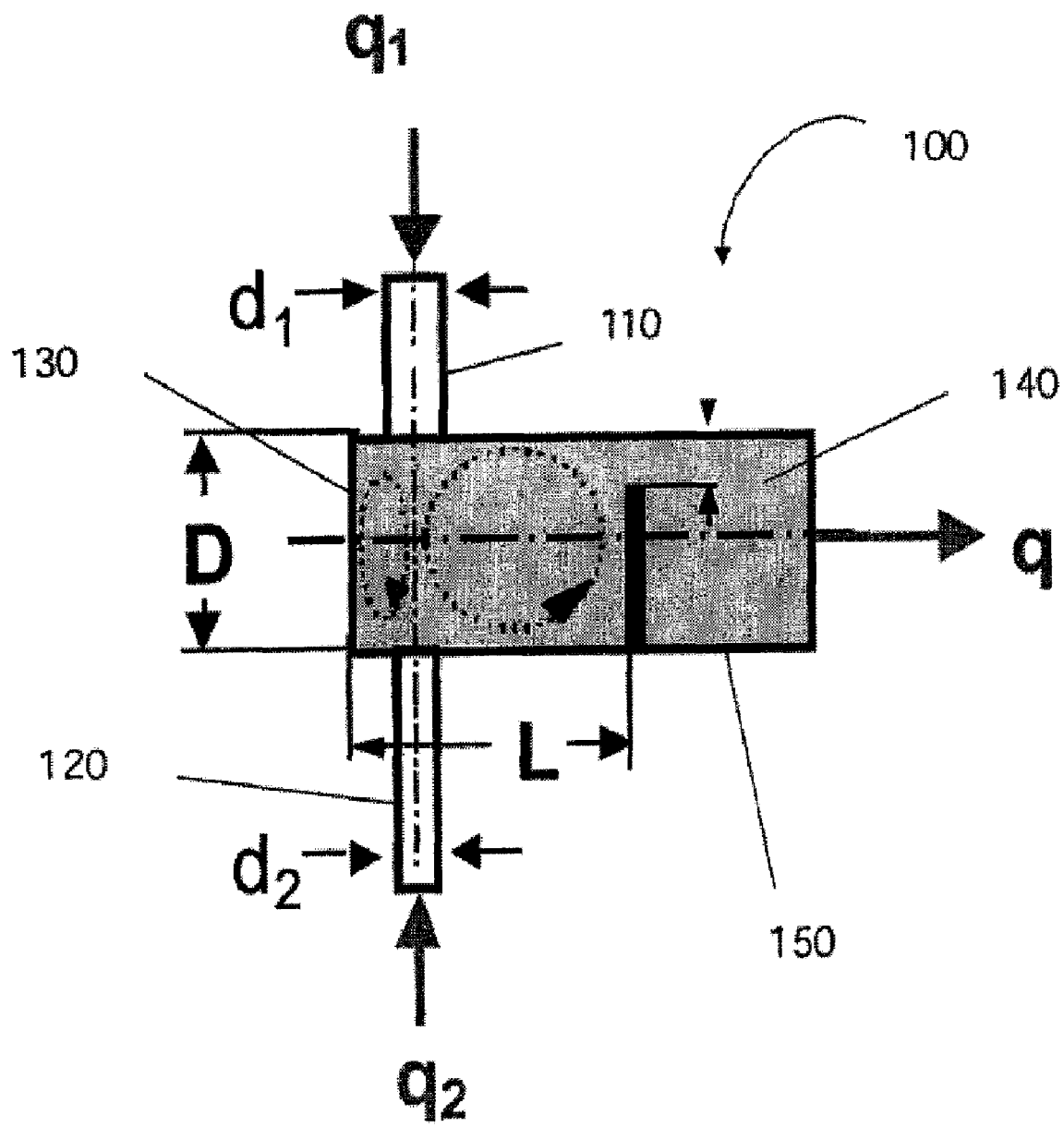
FIG. 3 shows a very schematical cross sectional view of a mixing chamber for performing step a) of the present invention according to a third embodiment of the present invention.

FIG. 3 shows a very schematically cross sectional view of the jet mixer for performing step a) of the present invention according to a third embodiment of the present invention. The system 100 comprises two inlets 110, 120 for the peptide solution (as indicated by q1) and the precipitation aid (q2), respectively. The inlets have a diameter d1, d2, respectively It is especially preferred that the ratio d1 (the inlet of the peptide solution) to D (which is the width of the mixing chamber) is $\geq 0.1:1$ and $\leq 0.4:1$, more preferred $\geq 0.2:1$ and $\leq 0.3:1$.

It is especially preferred that the ratio d2 (the inlet of the precipitation aid) to D (which is the width of the mixing chamber) is $\geq 0.05:1$ and $\leq 0.3:1$, more preferred $\geq 0.08:1$ and $\leq 0.13:1$.

As can be seen in FIG. 3, inside the jet mixer is formed a mixing zone 130 by the installation of an orifice, which covers approx. ¾ of the width of the mixing tube 150. As can be seen in FIG. 3, there will be a macroscopic convection flow with high turbulences in the section 130 (due to the counteracting liquid jets) whereas in the tube 140 far from the orifice less turbulences are produced. The mixture of the peptide solution and the precipitation aid is then delivered either to an heat exchanger or to the precipitation vessel as indicated by "q".

Figure 4:
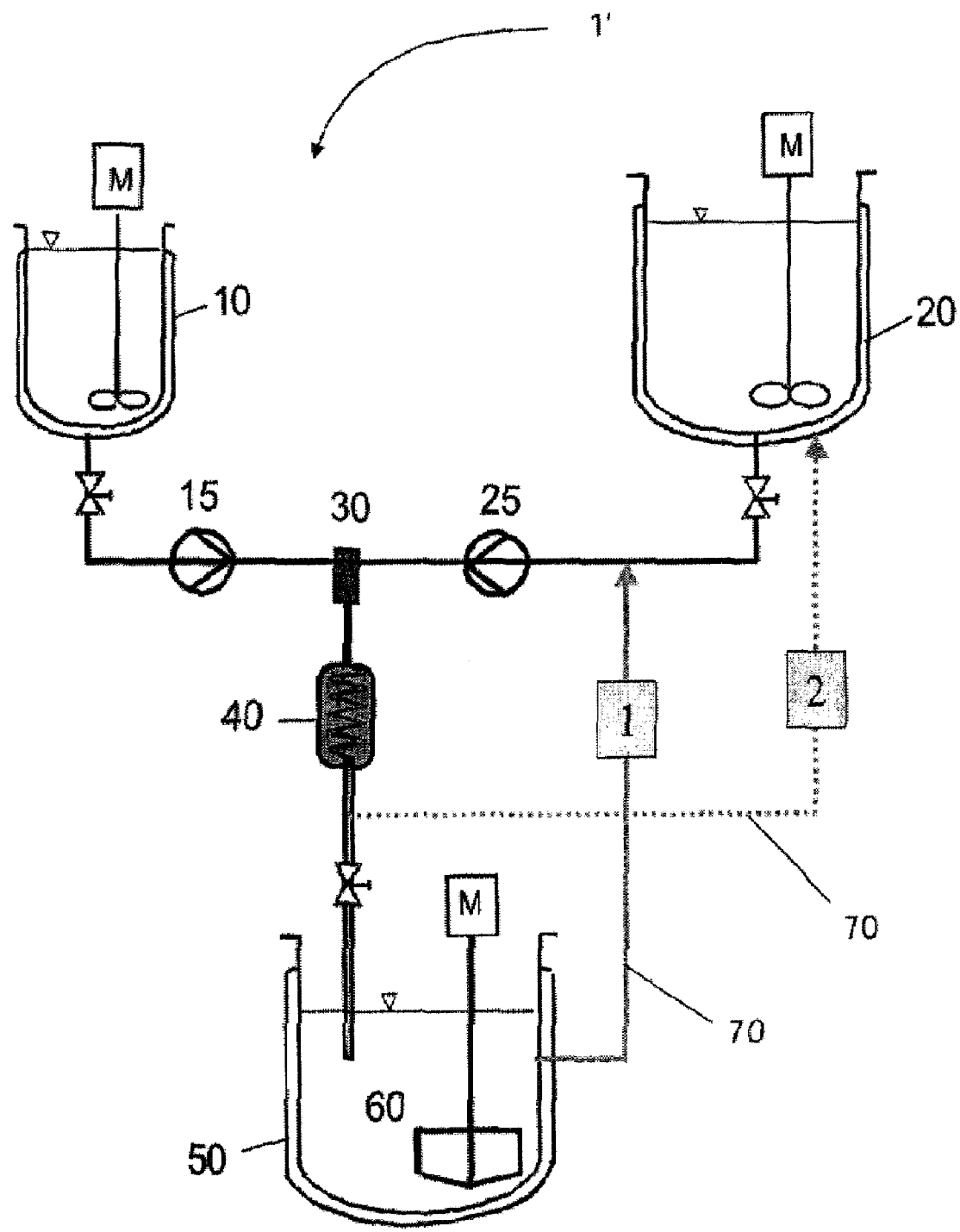
FIG. 4 shows a very schematical view of a device for performing the method according to the invention according to a fourth embodiment of the present invention.

FIG. 4 shows a very schematical view of a device 1' for performing the method according to the invention according to a fourth embodiment of the present invention. This device 1' is quite similar to the device of FIG. 1 except that two lines 70 for performing the recirculation mode are provided. In this particular embodiment Two types of re-circulation are proposed:

Mode 1:

After the first mixing of precipitant and protein only the ripening vessel 50 is used for the second and further re-circulations (using only re-circulation line "1" in FIG. 4). Therefore, the final precipitant concentration of every re-circulation is not reached immediately and a larger variation of precipitant concentration takes place than in case of mode 2 for a wide range of applications within the present invention Mode 2:

In this mode the ripening vessel 50 and the vessel 20, which first contains the protein solution, is alternatively used for the mixture. After the first mixing of precipitant and protein solution the mixture of the second re-circulation is transported in the complete empty protein vessel 20. During the third re-circulation run ripening vessel 50 is used again, and so on (using re-circulation lines "1" and "2" in FIG. 4). In this mode the precipitant concentrations are obtained immediately and well defined and no concentration fluctuations occur.

Compared to re-circulation mode 1 a smaller distance to the saturation curve can be realized for a wide range of applications within the present invention.

Figure 5:
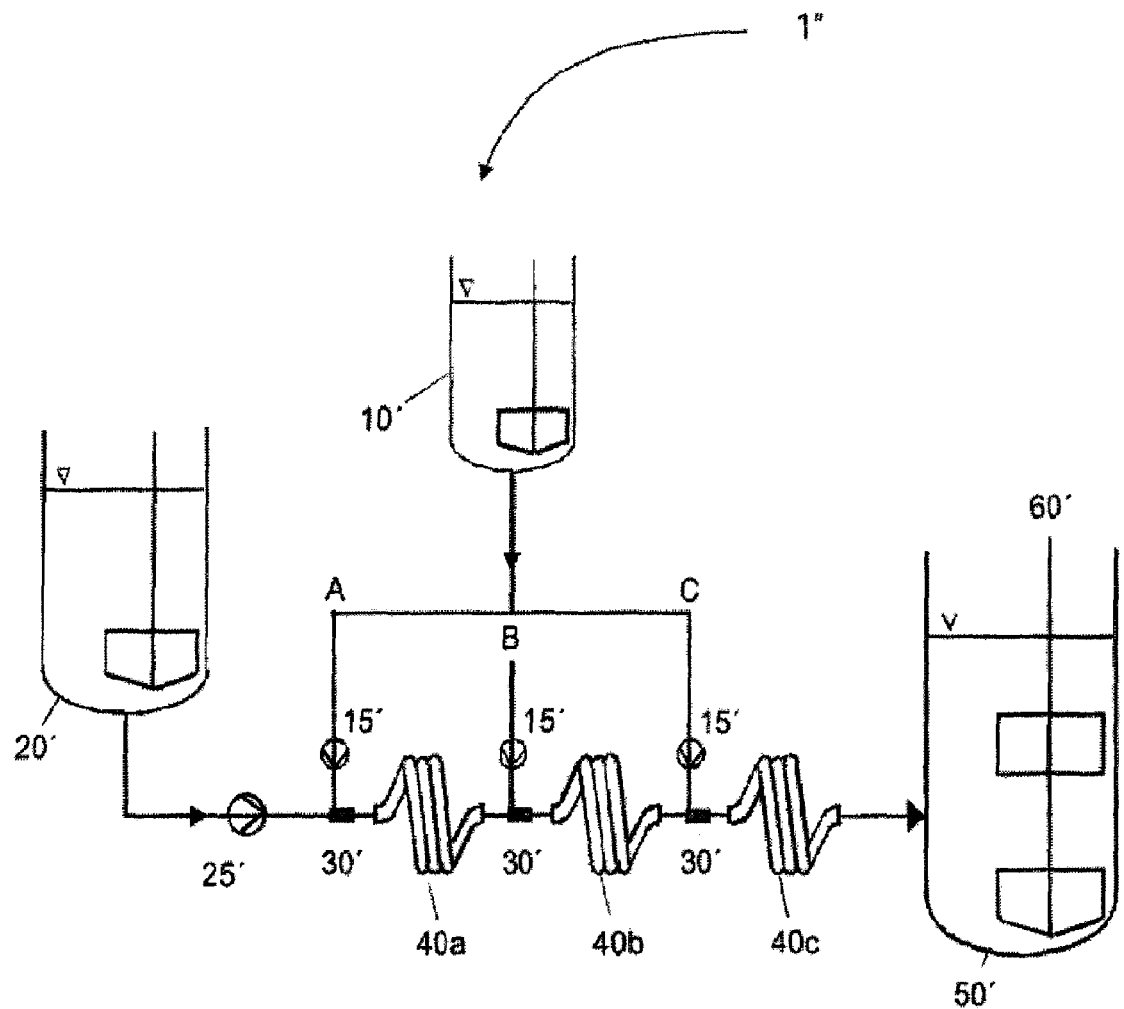
FIG. 5 shows a very schematical view of a device for performing the method according to the invention according to a fifth embodiment of the present invention.

FIG. 5 shows a very schematical view of a device 1" for performing the method according to the invention according to a fifth embodiment of the present invention. This device comprises the first vessel 10' where the precipitation aid is provided and the vessel 20' which contains the peptide solution. Both vessels are connected with pumps 15' and 25', jet mixers 15', where the step a) of the method is performed, with the ripening vessel 50' via helical tube reactors 40a, 40b, 40c, etc. producing the first protein agglomerates under very uniform flow conditions. The helical tube reactor could also used as heat exchanger for heat removal so far it is required. Vessel 50' in this embodiment is equipped with two blade agitators 60', although this not particular of importance for this special embodiment. This device is layed out for a "stepwise" precipitation (as indicated by "B" in FIG. 2).

Figure 6:
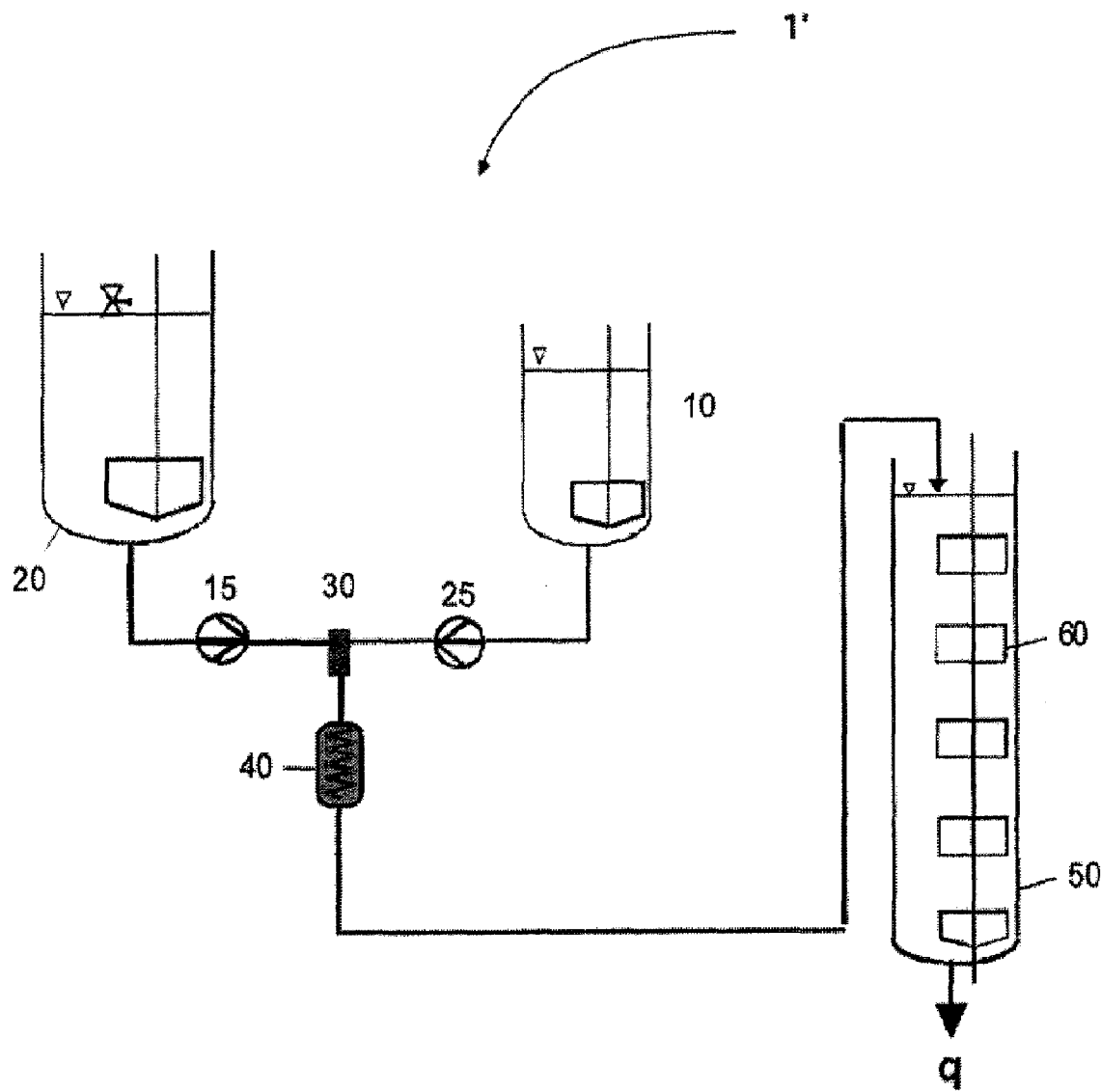
FIG. 6 shows a very schematical view of a device for performing the method according to the invention according to a sixth embodiment of the present invention.

FIG. 6 shows a very schematical view of a device 1' for performing the method according to the invention according to a sixth embodiment of the present invention. This device 1' is quite similar to that of FIG. 1, except that it is equipped for performing a continuos process. This means, that the ripening vessel 50 is provided in form of a lengthy vessel and the blade agitator 60 comprises several blades for performing a multi-step stirring process which leads to a very narrow residence time distribution and therefore to a very similar residence times of the fluid elements inside the precipitation reactor. This device follows the mode A (as indicated by "A" in FIG. 2).

According to a further embodiment (not shown in the figs), lines q1 and/or q2 may be provided, which lead to the vessels 10 and 20 respectively. By doing so also some recirculation may take place as described above.

Figure 7:
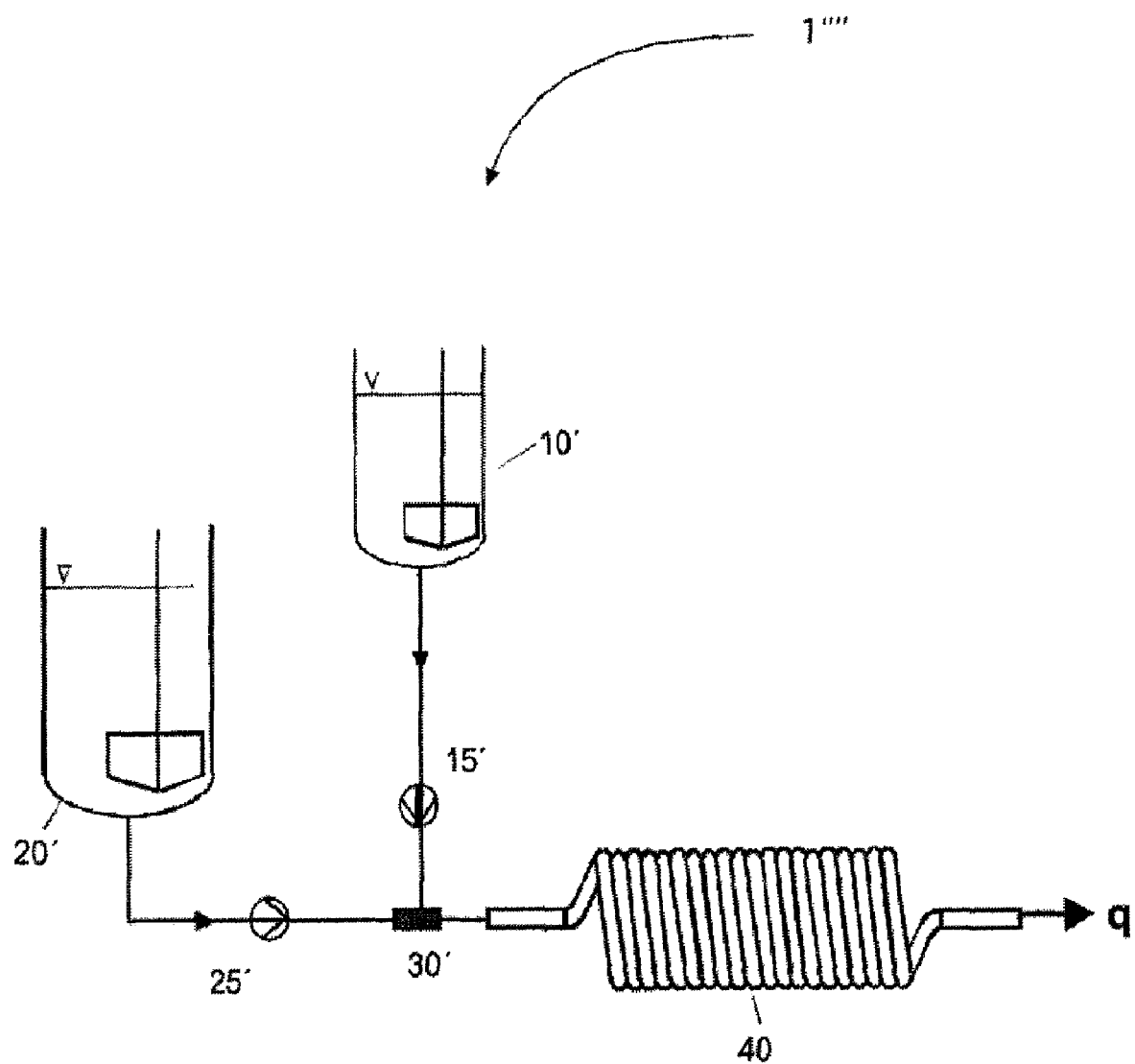
FIG. 7 shows a very schematical view of a device for performing the method according to the invention according to a seventh embodiment of the present invention.

FIG. 7 shows a very schematical view of a device 1"" for performing the method according to the invention according to a seventh embodiment of the present invention. In this embodiment, an extra ripening vessel is omitted, rather the precipitation takes place inside the helical tube reactor which can also been used as heat exchanger 40. The helical reactor has also a very narrow residence time distribution and therefore to a very similar residence times of the fluid elements inside the tube reactor. This device is—as any skilled artisan will easily see—also laid out for a continuos mode (as indicated by the "q"). This device follows the mode A (as indicated by "A" in FIG. 2).

According to a further embodiment (not shown in the figs), lines q1 and/or q2 may be provided, which lead to the vessels 10 and 20 respectively. By doing so also some recirculation may take place as described above.

Figure 8:
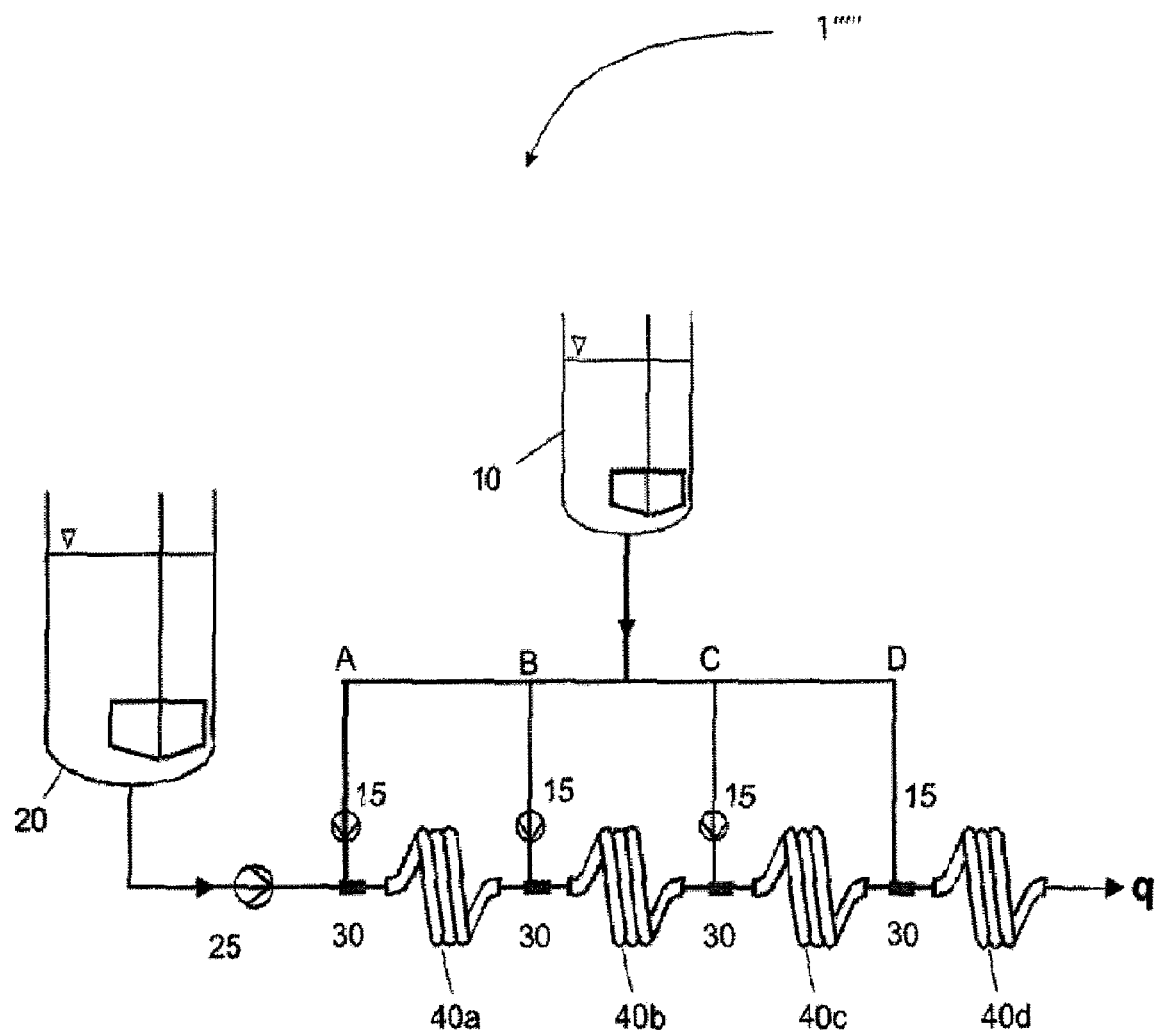
FIG. 8 shows a very schematical view of a device for performing the method according to the invention according to an eighth embodiment of the present invention.

FIG. 8 shows a very schematically view of a device 1'''' for performing the method according to the invention according to an eight embodiment of the present invention. In this embodiment, too, an extra ripening vessel is omitted and this device is—as any skilled artisan will easily see—also laid out for a continuos mode (as indicated by the "q").

However, this device is layed out for a "stepwise" precipitation, as indicated by "B" in FIG. 2. For this reason, several helical reactors 40a-40 d are provided, before each of them a defined amount of precipitation aid is added through lines A-D. This helical reactors may also used as heat exchanger.

According to a further embodiment (not shown in the figs), lines q1 and/or q2 may be provided, which lead to the vessels 10 and 20 respectively. By doing so also some recirculation may take place as described above.

EXAMPLE I

The present invention will be more understood using the following example, which—in a merely illustrative fashion—shows the precipitation of a protein out of a solution using a device and method according to the present invention.

The precipitation was performed in a device according to FIG. 1 of the present invention, using a 100 litre ripening vessel 50. For the delivery of the protein solution, a low-shear pump was used.

The jet mixer was set up according to FIG. 3, using two inlets with $d_1$=2.5 mm and $d_2$=6 mm, ending in a mixing chamber with a width of D=24 mm diameter. The jet mixer was used in such a fashion that a turbulent mixture with a Reynolds-Number of Re=1500 was achieved. Using this jet mixer by turbulent flow conditions, a mixing time of 65 ms was feasible.

After the jet mixer, an heat exchanger with an heat exchange area of A=0.35 $m^2$ was employed.

The throughput of precipitation aid (acetate buffer and ethanol) was $q_1$=68 l/h, protein solution (plasma solution according to Cohn, see ref. above) $q_2$=756 l/h. The pH-value inside the ripening vessel was 7.12<pH<7.28 with a temperature around −3° C.

The ripening vessel used had a diameter of $D_R$=406 mm equipped with a blade agitator having a blade height:diameter ratio of $h/d_R$=0.5. The blade agitator had six blades, having a ratio of agitator: vessel diameter $d_R/D$=0.55. The relative distance from the blade to the vessel was $e/D_R$=0.025.

The mixture of precipitation aid and protein solution was introduced into the vessel by a lance close to the bottom of the vessel having an conical angle (as described above) of about 5°, so that the incoming power of the stream was less than 0.3 $W/m^3$.

The precipitation led to the following results:

Fibrinogen could be separated from the other proteins in a much higher amount (test results gave about 50%) than in standard procedures. Further proteins, such as IgG, α1-Antitrypsin, Plasminogen and Albumin could only be found in the protein solution, i.e. essentially no co-precipitation took place.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. A method for the precipitation of peptides, comprising the steps:
   a) a first mixing step of an aqueous peptide solution with a precipitation aid, whereby an average mixing velocity of >0.05 m/s and <5 m/s is achieved in this step using a jet mixer; and
   b) a precipitation step in order to precipitate the peptide; whereby steps a) and b) are carried out spacially separated from each other.

2. The method according to claim 1, whereby in step a) [Delta]p is >0.05 bar and <20 bar.

3. The method according to claim 1, whereby the macroscopic mixing time in step a) is >1 ms and <1000 ms.

4. The method according to claim 1, whereby the macroscopic mixing time in step a) is >8 ms and <120 ms.

5. The method according to claim 1, whereby step b) is performed while continously agitating with a blade agitator.

6. The method according to claim 1, whereby step b) is performed while agitating with >0.1 W and <50 W.

7. The method according to claim 1, whereby the agitator is set with an extrentricity of >0 and <0.035.

8. The method according to claim 1, whereby the ratio of the blade diameter d to the diameter of the vessel and/or the compartment where step b) is performed is d:D >0.4:1 and <0.7:1.

9. The method according to claim 1, whereby the ratio of the vessel and/or the compartment where step a) is performed towards the vessel and/or the compartment where step b) is performed is >0.02:1 and <0.08:1.

10. The method according to claim 1, comprising a step a1) between steps a) and b): a1) performing a first precipitation and/or heat exchange in order to improve the precipitation and remove heat of mixing of step a).

11. The method according to claim 1, comprising a step c) after steps a) and b): c) constantly and/or discontinuously delivering a part of the solution of the precipitation suspension out of step b) to be co-admixed in step a).

12. The method according to claim 1, comprising a step a2) and a3) between steps a1) and b): a2) admixing further precipitation aid and a3) optionally repeating steps a1) and a2) ad lib.

13. A device for carrying out the method according to claim 1.

* * * * *

UNITED STATES PATENT AND TRADEMARK OFFICE
CERTIFICATE OF CORRECTION

PATENT NO. : 8,232,369 B2  Page 1 of 1
APPLICATION NO. : 12/520117
DATED : July 31, 2012
INVENTOR(S) : Henzler et al.

It is certified that error appears in the above-identified patent and that said Letters Patent is hereby corrected as shown below:

In the Specifications

Column 2, line 14, "precipated" -- should read -- precipitated --.

Column 6, line 47, "continuos" -- should read -- continuous --.

Column 7, line 1, "continuos" -- should read -- continuous --.

Column 7, line 10, "eight" -- should read -- eighth --.

Column 7, line 13, "continuos" -- should read -- continuous --.

Signed and Sealed this
Seventeenth Day of December, 2013

Margaret A. Focarino
*Commissioner for Patents of the United States Patent and Trademark Office*